United States Patent
Wollschlager

[11] Patent Number: 5,941,499
[45] Date of Patent: Aug. 24, 1999

[54] SEALING VALVE, IN PARTICULAR USED IN THE CATHETER TECHNIQUE

[76] Inventor: Helmut Wollschlager, Bühlstrasse 7, D-90482 Nürnberg, Germany

[21] Appl. No.: 09/011,126
[22] PCT Filed: Jul. 5, 1996
[86] PCT No.: PCT/DE96/01245
    § 371 Date: Jan. 16, 1998
    § 102(e) Date: Jan. 16, 1998
[87] PCT Pub. No.: WO97/03719
    PCT Pub. Date: Feb. 6, 1997

[30] Foreign Application Priority Data

Jul. 18, 1995 [DE] Germany .................. 195 26 075

[51] Int. Cl.⁶ ........................................ F16K 7/02
[52] U.S. Cl. .................................... 251/4; 257/7
[58] Field of Search ............................ 251/4, 7

[56] References Cited

U.S. PATENT DOCUMENTS

| | | | |
|---|---|---|---|
| 3,685,786 | 8/1972 | Woodson | 251/4 |
| 4,917,668 | 4/1990 | Haindl | 604/167 |
| 5,529,278 | 6/1996 | Weldon et al. | 251/4 |

FOREIGN PATENT DOCUMENTS

| | | |
|---|---|---|
| 0 135 140 | 3/1985 | European Pat. Off. . |
| 0 267 584 | 5/1988 | European Pat. Off. . |
| 0 534 000 A2 | 3/1993 | European Pat. Off. . |
| 0 546 712 A2 | 6/1993 | European Pat. Off. . |
| WO 94/14497 | 7/1994 | WIPO . |

*Primary Examiner*—John Fox
*Attorney, Agent, or Firm*—Baker & Daniels

[57] ABSTRACT

The invention concerns a sealing valve which comprises a valve body (1) on which a sealing cylinder (8) is mounted. The sealing cylinder (8) contains a sealing stopper against which a pressure piston (18) abuts. A lever arm (23), which is loaded in terms of force by a spring component (31), presses on the pressure piston (18). The valve can be used within the scope of the interventional catheter technique for sealing a guide catheter. Advantageously it can be sensitively and topically actuated with one hand in an ergonomic manner.

12 Claims, 9 Drawing Sheets

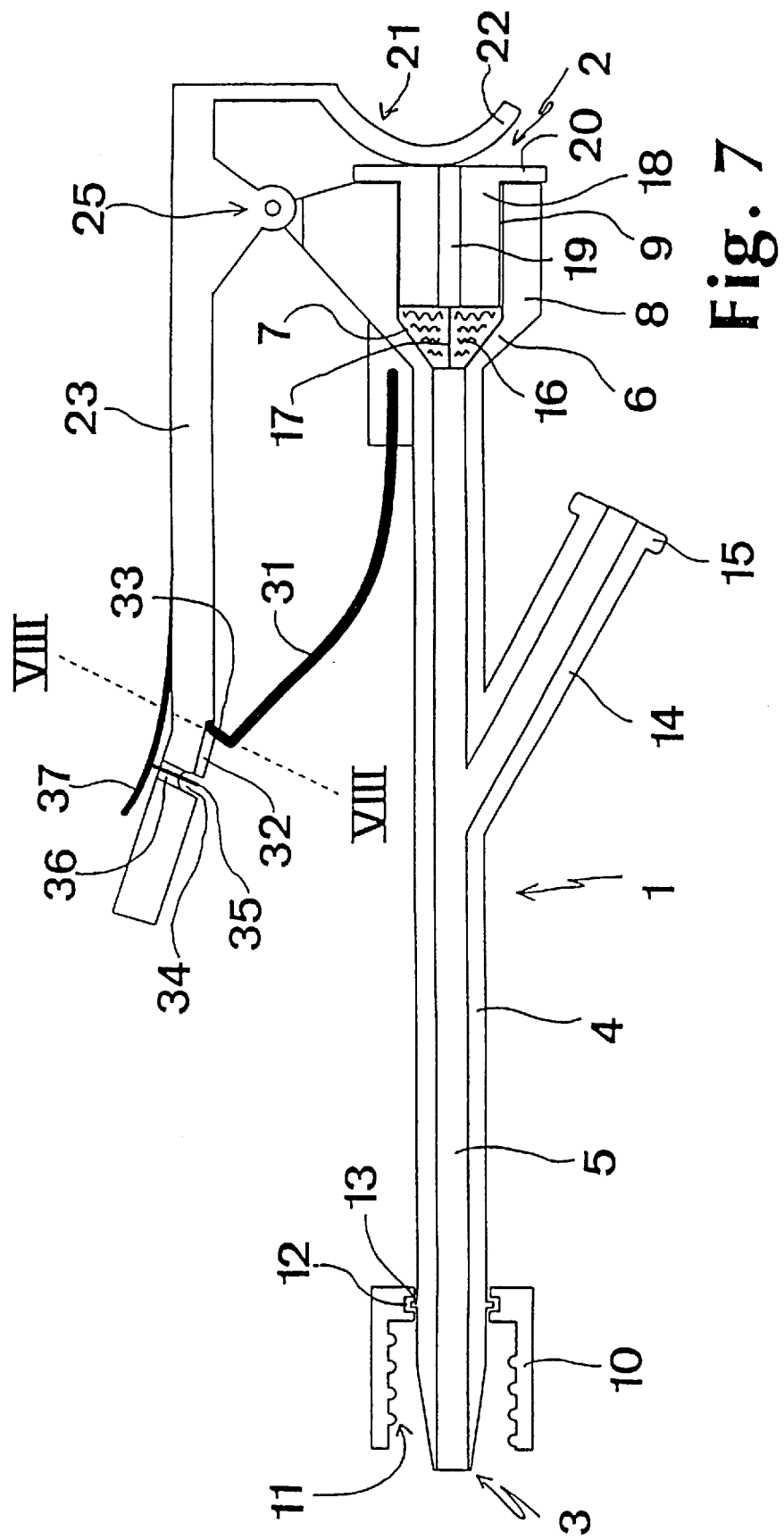
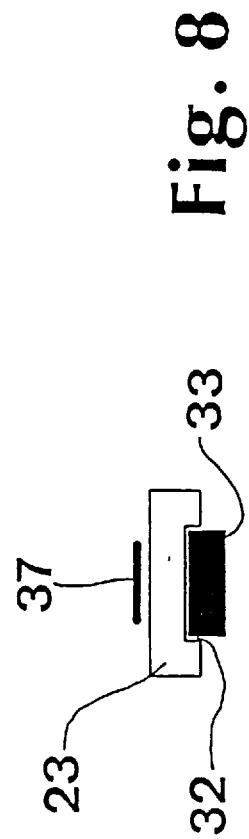
Fig. 7
Fig. 8

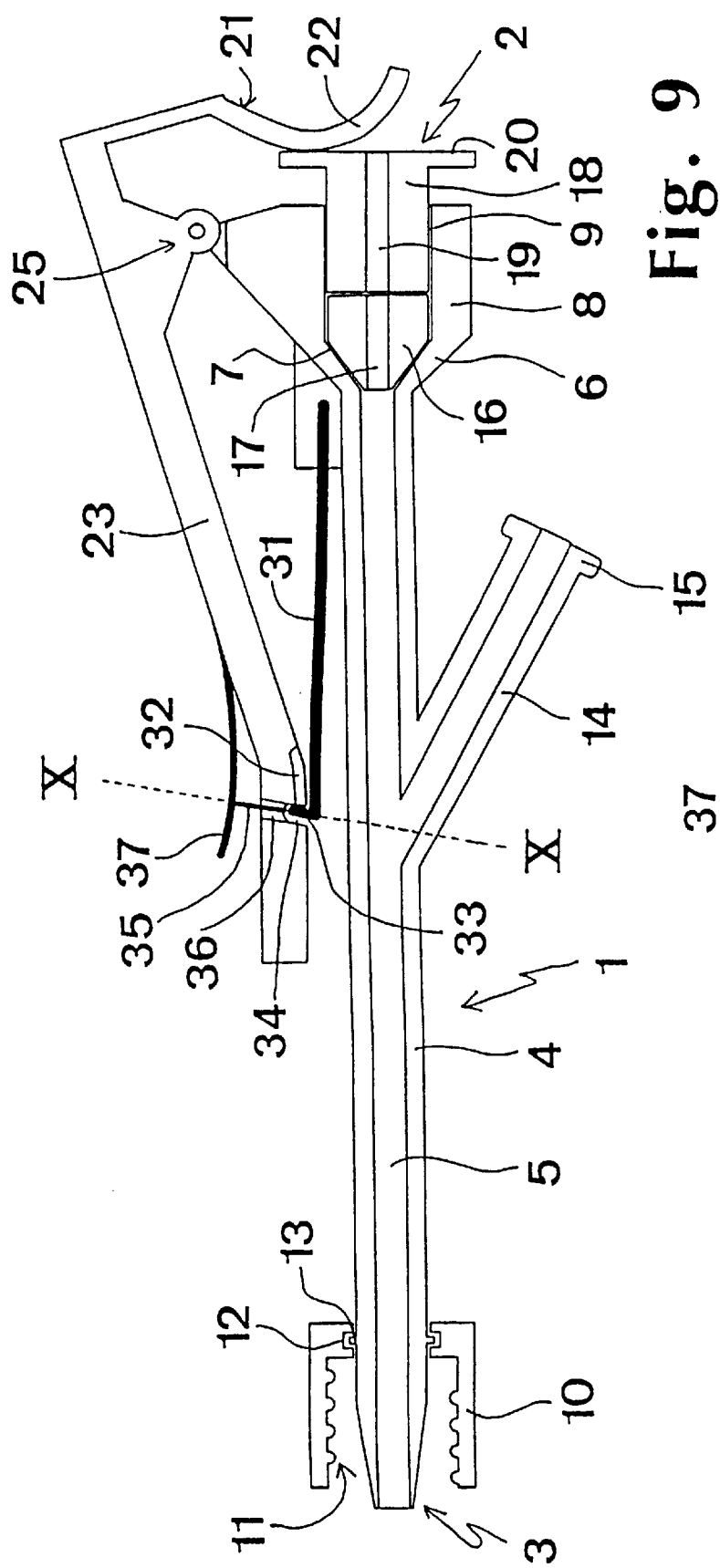
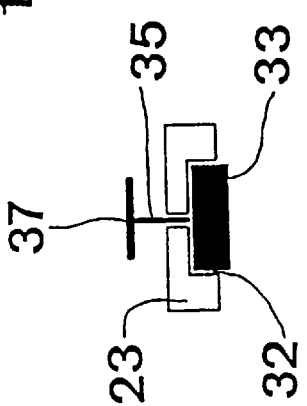
Fig. 9
Fig. 10

SEALING VALVE, IN PARTICULAR USED IN THE CATHETER TECHNIQUE

The invention relates to a sealing valve with a longitudinally extended valve body that exhibits a connective end and a sealing end, in which valve body a valve passageway is embodied that extends from the connection end to the sealing end in an axial direction, in which a sealing plug that may be compressed for the purpose of sealing is provided that is equipped with an axial plug passageway.

Such a sealing valve is known from the European patent document EP 0 267 584. The valve body of the known sealing valve exhibits a main tube that constitutes the connection end, onto which a sealing cylinder that constitutes the sealing end is set. The internal diameter of the sealing cylinder is greater than the internal diameter of the main tube. The transition from the inner chamber of the sealing cylinder to the passageway of the main tube is accomplished by means of a conically tapering shoulder section. Within the inner chamber of the sealing cylinder, an elastic sealing plug is found that abuts the conical shoulder section, which plug may be compressed with the aid of a plunger that may be moved in the axial direction, but is secured against rotations within the interior chamber of the sealing cylinder. The plunger is equipped, on the side facing the sealing end, with a spiral surface upon which an additional spiral surface of a lever closure that is imposed upon the sealing cylinder presses. In order to activate the valve, the lever closure is turned toward the sealing cylinder so that the spiral surfaces are shifted toward one another, and the plunger is moved in the axial direction. If the sealing plunger is compressed, the elastic material of the sealing ring moves out of the way toward the inside, and the plug passageway is reduced in size. By virtue of this fact, the sealing plug is able to seal off the sealing valve, or an instrument that is guided through the sealing valve.

Such a sealing valve is a crucial component of interventional catheter technique. This technique is used, for example, to expand narrowed coronary arteries with the aid of a balloon catheter. In order to bring the balloon catheter to that point of the coronary arteries that must be treated, a guide catheter must, first of all, be introduced through an opening in the patient's inguinal area, and advanced, via the aorta, to the origin of the artery to be treated. Thereafter, a wire having a diameter of a few tenths of a millimeter is introduced through this guide catheter into the blood vessel that is to be treated. Then, the balloon catheter is threaded onto this wire and advanced to the point to be expanded.

During these treatment steps, the guide catheter is sealed off by means of the sealing valve. When the instruments are introduced, the left hand of the physician rendering treatment holds the sealing valve while the right hand undertakes the movements that are necessary to maneuver the instruments, either opening or closing the valve as necessary in the interim. Because of the ungainly reaching around with the right hand that is necessary to activate the valve, the valve frequently remains unintentionally and unnecessarily opened, for which reason, among other things, the patient loses considerable amounts of blood. In certain circumstances, this state of affairs represents a threat to the patient. In any case, the field of instrumentation is soiled by considerable amounts of blood.

Furthermore, from the United States patent document U.S. Pat. No. 4,917,668, a sealing valve is known that is comprised of a sealing body. The sealing body exhibits a connection piece that may be connected to a guide catheter, to which, in the axial direction, an introduction piece is connected. The connection piece and the introduction piece are equipped, in each case, with a central passageway which may be sealed off by means of an elastic sealing membrane, provided, in the area of the passageway, with slits, and clamped between the connection piece and the introduction piece. On the side of the sealing membrane that faces toward the connecting catheter, the sealing membrane is supported by a spring element provided in the connection piece that assures the closure of the sealing membrane if no object that must be sealed is located within the passageway. On the side of the sealing membrane that faces away from the catheter to be connected, there is a tappet with a central passageway, which tappet is mobile in the axial direction, toward the sealing membrane and is held, in the at rest position, by an additional spring element at some distance from the sealing membrane. To open the sealing valve, a guide tube is pushed into the introducing portion, which tube pushes the tappet through the sealing membrane. A catheter may then be advanced through the sealing membrane that is opened in this manner and through the passageways of the sealing body into the guide catheter that is applied to the connecting portion of the sealing body.

A check valve for medical purposes that exhibits a cup-like valve housing is known from the European patent document EP 0 135 140. A spiral spring is applied at the bottom of the cup that presses a valve slide against a sealing stop that is provided in the area of the opening of the cup. The slide, whose position may be shifted in an axial direction within the valve housing, with its circumferential surface, is guided over a valve opening that is provided in the wall of the valve housing, which leads to a channel groove that is introduced to the outside of the valve housing, which groove runs in an axial direction. To open the valve, the slide is pushed in the direction of the bottom of the cup until the slide uncovers the valve opening in the wall of the valve housing and the fluid that is to be sealed off can flow from the opening of the cup of the valve housing through the valve opening and the channel groove into a catheter that surrounds the valve housing.

Taking this state of the art as a point of departure, it is the underlying task of the invention to create a sealing valve that can be activated with one hand in an ergonomic manner in a sensitive and timely way.

This task is resolved by virtue of the fact that in order to compress the sealing plug, a spring element is provided that may be neutralized in its effect by means of an activation mechanism.

By virtue of the fact that the force for the compression of the sealing plug is applied by a spring element, the sealing valve can be opened and closed quickly. In addition, it is assured that the sealing valve closes automatically when the activation mechanism is released.

In the case of one preferred embodiment, a lever arm that runs longitudinally relative to the valve body, and is swivel-mounted on the valve body with a pressure fork that is applied to the lever arm at a right angle, presses upon a pressure piston that abuts the sealing plug that engages the passageway of the valve body. The elastic force is applied by means of a spring element that is stretched between the lever arm and the valve body.

This sealing valve can be held, in relaxed fashion, with one hand, in most cases, the left hand. In the process, the index finger, the middle finger, and the ring finger lie on the lever arm and press the sealing valve against the thumb that lies against the opposite side of the valve body. By pressing the index, middle, and ring finger on one side, and the thumb on the other side together, the valve can be activated in an ergonomic fashion by means of a single movement with one hand.

Due to the fact that this sealing valve is a disposable article that is produced in great quantities, the space required for its storage is a critical consideration. In the case of this sealing valve, the lever arm is provided longitudinally, relative to the body of the valve. In this way, the required storage volume is small, even in the case of a lever arm of great length.

However, with a great length of the lever, it is possible to achieve the requisite sensitivity during opening and closing.

In what follows, advantageous embodiments of the invention will be described by virtue of the drawing.

FIG. 7 shows a further embodiment of the sealing valve;

FIG. 8 shows a cross-section through the arm of the lever along the line of intersection VIII—VIII in FIG. 7;

FIG. 9 shows a longitudinal frontal view through the sealing valve from FIG. 7, in the opened state;

FIG. 10 shows a cross-section through the arm of the lever, along the line of intersection X—X in FIG. 9;

Figure 1:
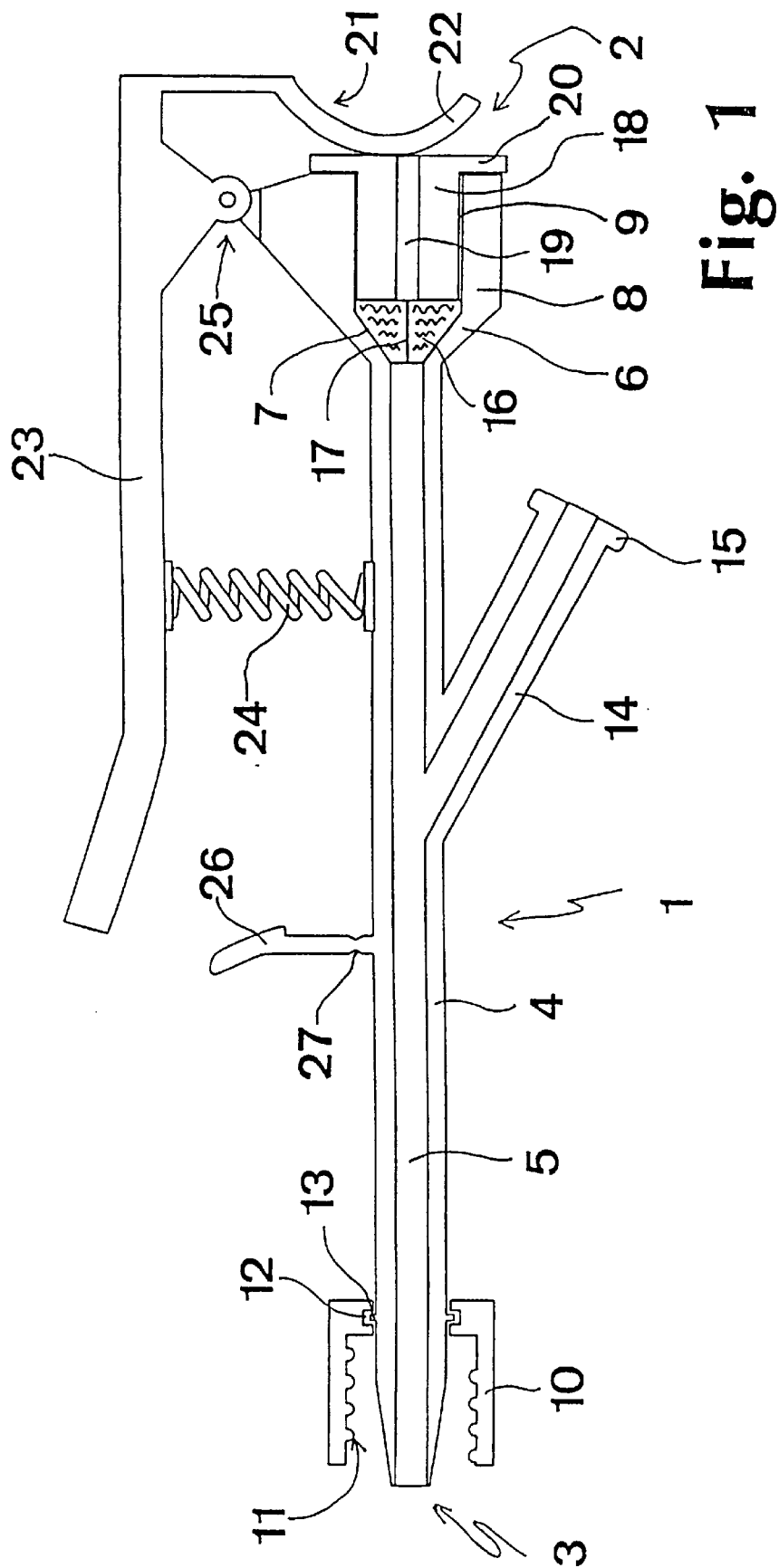
FIG. 1 shows a view, in longitudinal section, of a sealing valve, in closed state.

FIG. 1 shows a cross-sectional view of the sealing valve that exhibits a valve body 1 with a sealing end 2 and a connecting end 3. The valve body 1 has at its disposal a main tube 4 with an axial passageway, 5. A sealing cylinder, 8, with an inner chamber 9, is positioned onto the main tube, 4, by way of a conical expansion, 6, with a conical interior surface, 7. At the connective end, 3, the main tube, 4, is slanted in conical fashion in order to render connection to a guide catheter possible. In addition, at connective end 3, a threaded sleeve, 10, is found, which may be screwed onto external threading of the guiding catheter by way of internal threading, 11. A seal that is indicated in the drawing by means of an annular groove 12 and an annular spring, 13, assures a tight connection of the sealing valve with the guiding catheter. At a distance from connective end 3, laterally with respect to the main tube 4, at an acute angle to the main tube, 4, a lateral tube 14, is positioned, that may be connected, by way of a flange, 15, for example, to a pressure measurement device. An elastic sealing plug 16 abuts the conical inner surface 7 of the conical extension 6, which plug has the form of a cylinder with a superimposed cone. An axial passageway, 17, through the plug, is embodied within the sealing plug 16. In the closed position that is depicted in FIG. 1, the sealing plug 16 is compressed by a compression piston, 18, and plug passageway 17 is closed. Like the sealing plug, 16, compression piston 18 also has at its disposal an axial piston passageway, 19. On compression piston 18, toward the outside, a pressure plate, 20, that constitutes a stop is embodied against the sealing cylinder, 8. A pressure fork, 21, with bent tines, 22, presses upon the pressure plate, 20. The pressure fork, 21, is set at right angles with respect to a lever arm, 23, that is arranged laterally in the longitudinal direction with reference to the main tube, 4. If lever arm 23 moves, the tines, 22, of the pressure fork 21 roll off on pressure plate 20. A helical compression spring, 24, is stretched between the lever arm, 23, and the main tube, 4. For the sake of clarity, the helical compression spring, 24, is not depicted in cross-section, but rather, in a lateral view. The lever arm, 23, is mounted on a bearing above a hinged joint 25 that is provided in the area of sealing end 2 so that it is capable of being swiveled. The helical compression spring, 24, presses the lever arm, 23, away from the main tube 4, and thus, the tines, 22, of the pressure fork, 21 press upon the pressure plate, 20 of the compression piston, 18, which compresses the sealing plug, 16. The material of the elastic sealing plug, 16, led by the conical inner surface, 7 swerves toward the inside, thus closing the passageway through the plug, 17. An instrument that is led through the passageway through the plug, 17, is thus sealed off in this way.

Figure 2:
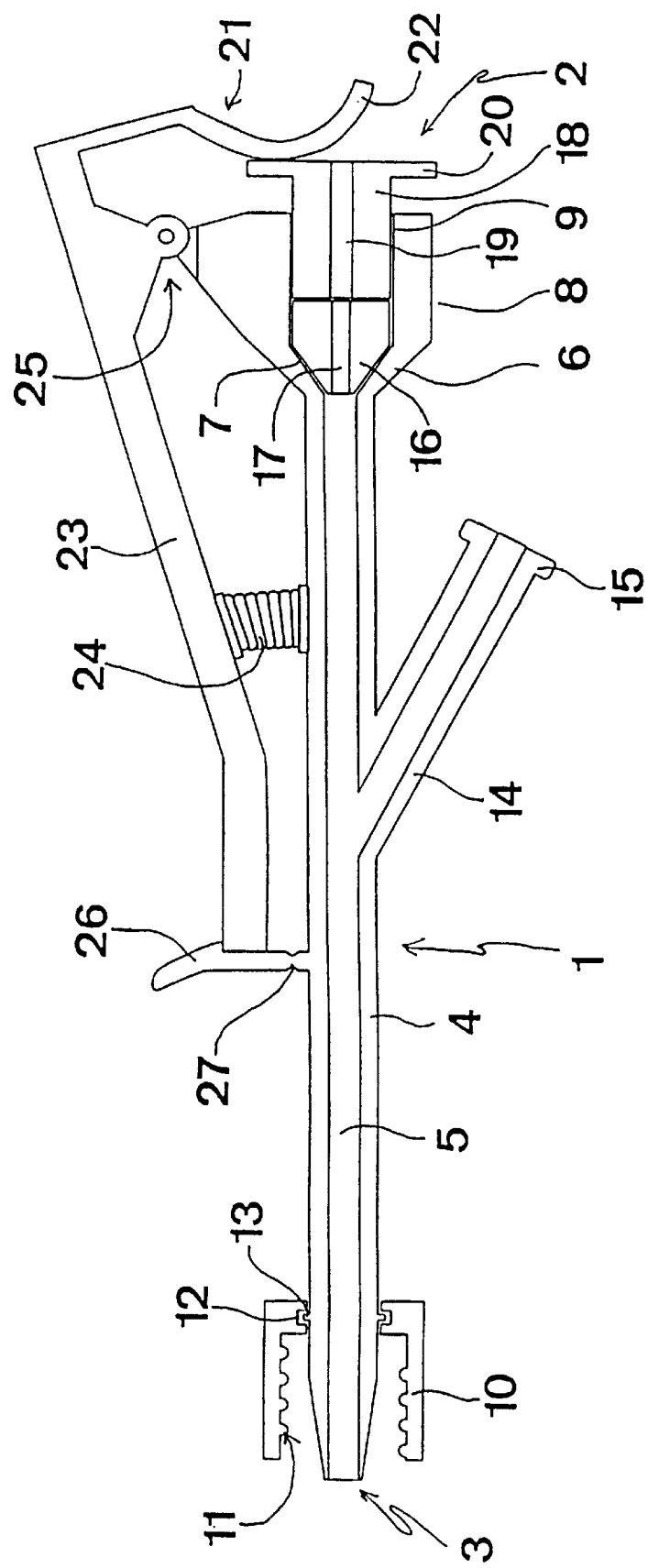
FIG. 2 shows a view, in longitudinal section, of the sealing valve, in the opened state.

FIG. 2 shows the sealing valve from FIG. 1, in the opened state. The helical compression spring, 24, is compressed, and the end of the lever arm, 23, is arrested with the aid of a snap hook, 26. The snap hook, 26, that is applied to the main tube, 4, exhibits a bending taper, 27. As a result of this bending taper, 27, the snap hook, 26, may be retracted, and the lever arm, 23, can be released from the stop. Thus, by activating lever arm 23, the effects of helical compression spring 24 can be neutralized.

It should be noted that in the case of a derived embodiment example that is not depicted in the drawing, the snap hook, 26, is embodied so as to have two or more stages. Such an embodiment of the snap hook, 26, enables the user to open or close the valve by stages.

Figure 3:
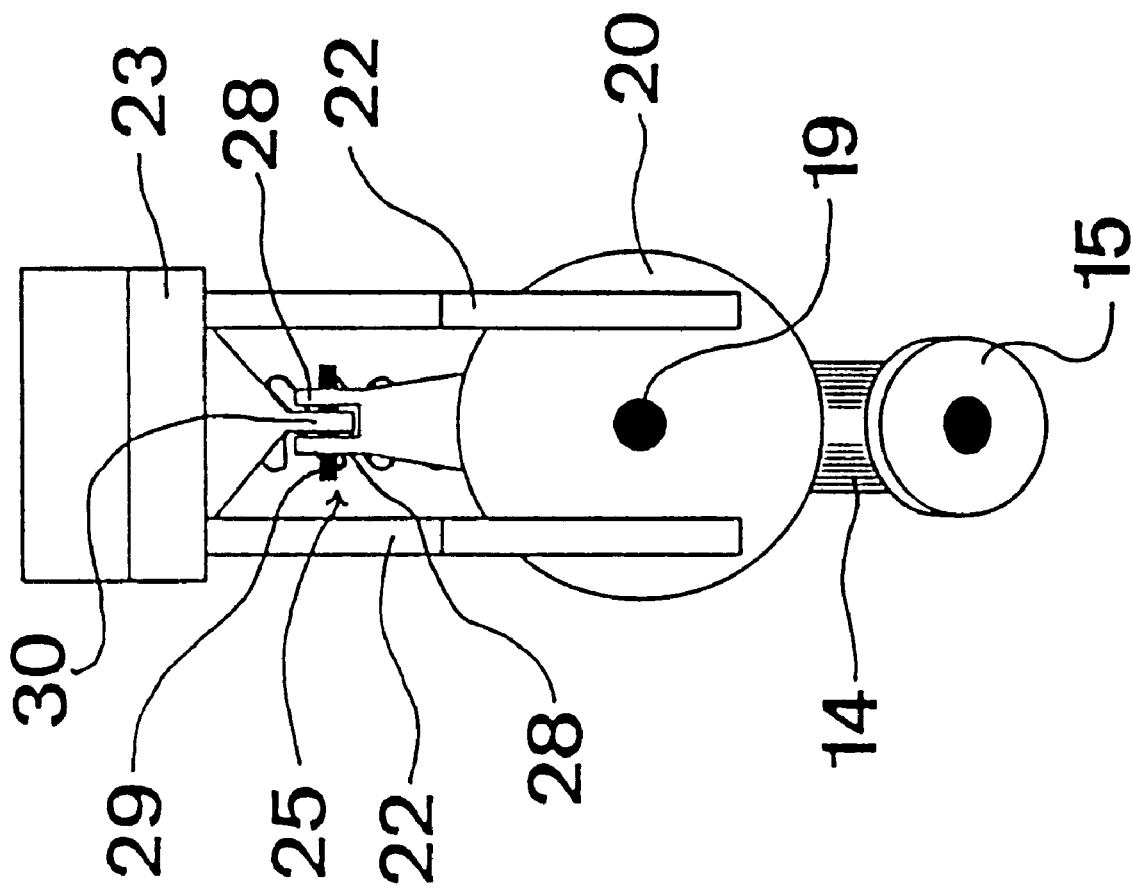
FIG. 3 shows a view from the back of the sealing valve from FIGS. 1 and 2, in the closed state.

FIG. 3 shows a view of sealing end 2 of the sealing valve. One can clearly distinguish the pressure plate 20 with the central piston passageway, 19. In addition, the tines, 22, of pressure fork, 21, which abut pressure plate 20 on either side of the piston passageway 19, are discernible. Between the tines, 22, of pressure fork, 21, a hinged joint, 25, may be seen. Two articulated struts, 28, applied to the compression cylinder, 8, hold an articulated pin, 29. An articulated grommet, 30, that is applied to the lever arm, 23, engages between the articulated struts, 28, which grommet is mounted on a bearing on the articulated pin, 29, in such a way as to be capable of being swiveled. The helical compression spring, 24, may be discerned behind the articulated hinge, 25.

In order to support the lever arm, 23, laterally, in the case of a derived embodiment example that is not depicted in the drawing, the articulated struts, 28, and the articulated grommet, 30, are extended in the longitudinal direction, so that ridge-shaped articulated struts form a groove into which a ridge-shaped articulated grommet engages.

The sealing valve that is depicted in FIGS. 1 through 3 is applied, above all, within the context of interventional catheter technique. For example, in order to expand constrictions of the coronary arteries with the aid of a balloon catheter, the balloon catheter must be brought to the site of the coronary arteries. To do so, a stable guide catheter having a relatively large lumen of up to ten French (=three millimeters) is introduced through an opening in the region of the patient's groin, by way of the aorta to the opening of the coronary artery that is to be treated. The guide catheter is sealed off by means of the sealing valve according to the invention. After that, a thin guide wire of one French (=one-third of a millimeter) in diameter is introduced through the sealing valve and the guide catheter, far into the coronary artery to be treated. By way of this wire, then, the balloon catheter, which serves to effect the actual treatment, is threaded on and advanced to the point of expansion. During the entire treatment, the guide catheter is sealed off from the high blood pressure in the aorta (150 mm on a mercury column, which is approximately equal to 0.2 bar) by means of a sealing valve according to the invention.

It should be noted that guidance catheters having a lumen of up to 14 French (=4.2 millimeters) in diameter are used in radiology to expand blood vessels. Even these types of guidance catheters can be sealed using the sealing valve according to the invention.

During treatment, the treating physician's left hand holds the sealing valve while the right hand completes the movements necessary to maneuver the instruments. The sealing valve can be operated in a particularly ergonometric fashion if the sealing valve is held between the thumb in one instance, and the index, middle, and ring finger in the other. Gripped in this way, only the index, middle, and ring fingers need to be bent slightly in order to hold the sealing valve. To close the sealing valve, the index, middle, and ring finger are pressed against the thumb in a single motion. Due to the fact that only a single motion of the hand is needed to activate the valve, it is possible to work in a relaxed manner.

In addition, the sealing valve can be operated in timely fashion. In undertaking treatment, for psychological reasons, the physician providing the treatment frequently has the impression that the instrument that is advanced into the vessel undergoing treatment is blocked by the seal of sealing valve, whereas, in reality, by contrast, the inhibiting friction is produced at a point in the patient's body. With a sealing valve that can be opened and closed quickly, the physician who is providing treatment can quickly ascertain the cause of the friction by opening the sealing valve slightly for a short time. If, by so doing, the resistance that inhibits the movement of the instrument does not decrease, the point that is causing the resistance is located within the body of the patient. The physician can verify this fact all the more readily if the sealing valve can be activated with a single hand, so that the time-consuming switching of hands from the instrument that must be maneuvered to the sealing valve is unnecessary.

A further advantage is that the sealing valve is closed in the at-rest state. Thus, the physician who is providing treatment can, if he needs a pause to rest, simply release the sealing valve without having to undertake additional maneuvers to close the sealing valve.

The sealing valve is, to good advantage, embodied as a disposable object. Accordingly, the majority of the structural elements of the sealing valve consist of plastic. If it is necessary for the transfer of force, in addition to the helical compression spring, 24, other structural elements, such as the lever arm, 23, or the tines, 22, of the pressure fork, 21, are made of a metallic material.

Due to the fact that the pressure valve is produced in large numbers of units as a disposable article, it is advantageous if little space is required for purposes of storage. In the case of the sealing valve according to the invention, the lever arm 23 is provided alongside main tube 4. Consequently, even a long lever arm, 23, does not appreciably increase the volume needed for storage.

A long lever arm is necessary, however, in order to achieve the requisite sensitivity in activating the valve.

A series of derivations of the sealing valve according to the invention is conceivable.

Figure 4:
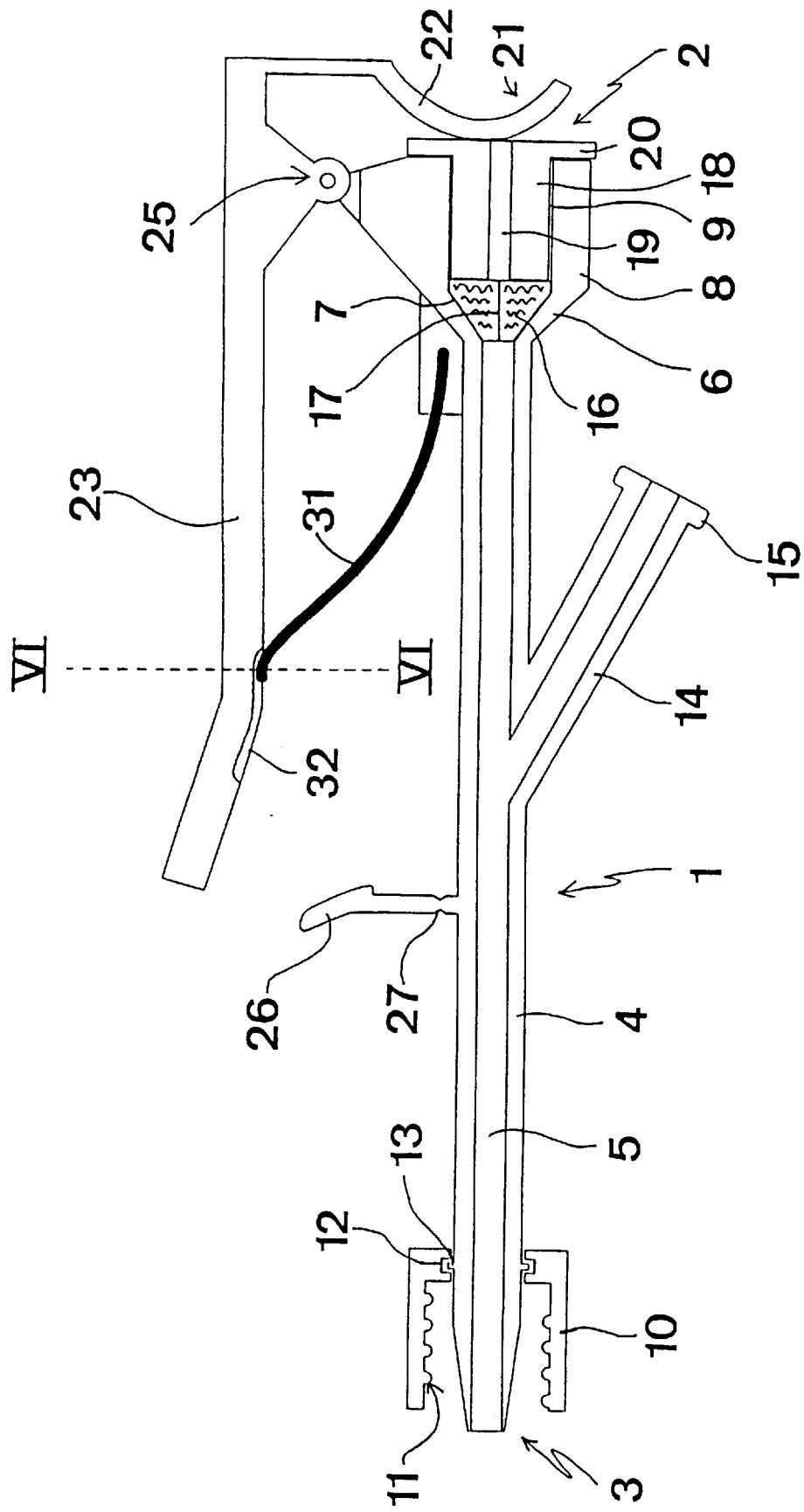
FIG. 4 shows a view, in longitudinal section, of an additional embodiment of the sealing valve, in the closed state.

FIG. 4 shows a sealing valve in which the helical compression spring, 24, is replaced by a leaf spring, 31. The leaf spring, 31, is attached to one end, in the area of sealing cylinder 8 on valve body 1, whereas the other end of the leaf spring, 31, glides within a guide groove, 32, that is embodied in the lever arm, 23.

Figure 5:
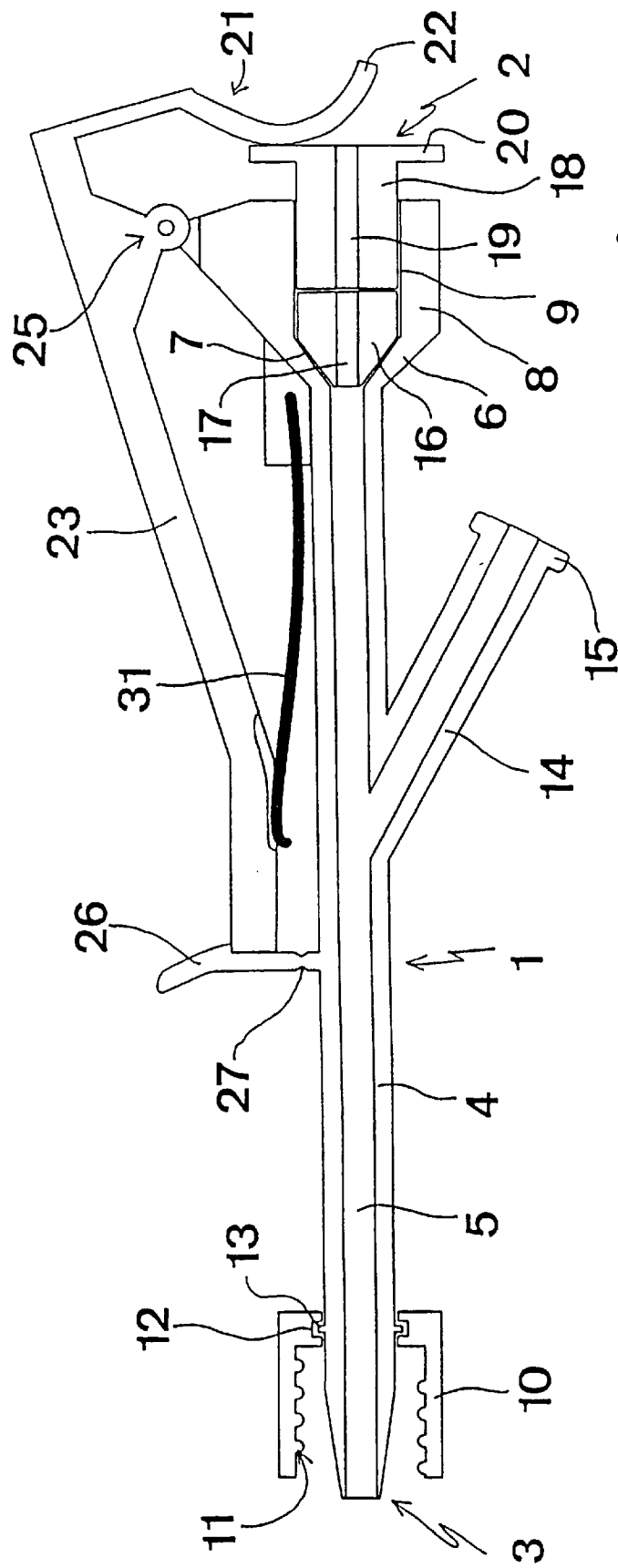
FIG. 5 shows a longitudinal sectional view of the sealing valve from FIG. 4, in the opened state.

FIG. 5 shows the embodiment example from FIG. 4 in the opened state. One can see that the lever arm, 23, as in the case of the embodiment example described by virtue of FIGS. 1 through 3, may be arrested by a snap hook, 26.

Figure 6:
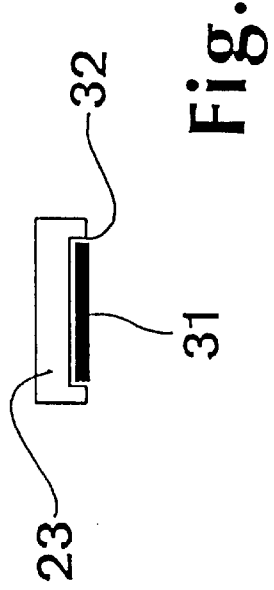
FIG. 6 shows a cross-section through the lever arm, along the line of intersection VI—VI in FIG. 4.

For purposes of greater clarity, FIG. 6 shows a cross-section through the lever arm 23 along the line VI—VI in FIG. 4. One recognizes the leaf spring, 31, which glides within guide groove 32. Above all, guide groove, 32 serves to prevent lateral movements of the lever arm, 23. If, as a result of this measure, sufficient lateral stability cannot be achieved, the guidance of the lever arm, 23, can be improved by virtue of the fact that the articulated struts, 28, as mentioned above, as well as the articulated grommet, 30, are extended in the longitudinal direction of the valve body 1, so that the lever arm, 23, is guided better laterally.

FIG. 7 shows an additional embodiment example of the invention. In the case of this embodiment example, at the end of the leaf spring, 31, that is turned toward the lever arm 23, a protruding ridge, 33, is embodied. The ridge, 33, glides within guide groove 32, which makes the transition, toward the end of the lever, to a rest depression, 34, that is introduced into lever arm 23. From the opposite side of the lever arm 23, a tappet, 35, engages rest depression 34 through tappet recess 36. The tappet, 35, may be activated by means of a release button, 37.

FIG. 8 shows a cross-section along the line VIII—VIII in FIG. 7.

FIG. 9 shows the embodiment example that is depicted in FIG. 7, with the sealing valve in its opened state. In this state, ridge 33 engages rest depression, 34, of the lever arm, 23. The tappet, 35, is pressed out of rest depression 34 and cocks the release button, 37, of the pressed lever arm, 23. By activating the release button, 37, it is possible to push the tappet, 35, into the rest depression 34, thus releasing the arresting of lever arm 23.

The release button, 37, is, to good purpose, produced from a blade spring so that the release button, 37, in the opened state of the sealing valve, can be activated with the expenditure of little energy.

In the case of a derived embodiment example, two or more rest depressions, 34, are embodied in lever arm 23, so that the sealing valve may be opened or closed in two or more steps.

For purposes of clarification, FIG. 10 shows a cross-section through the lever arm 23 along the line X—X in FIG. 9.

Figure 11:
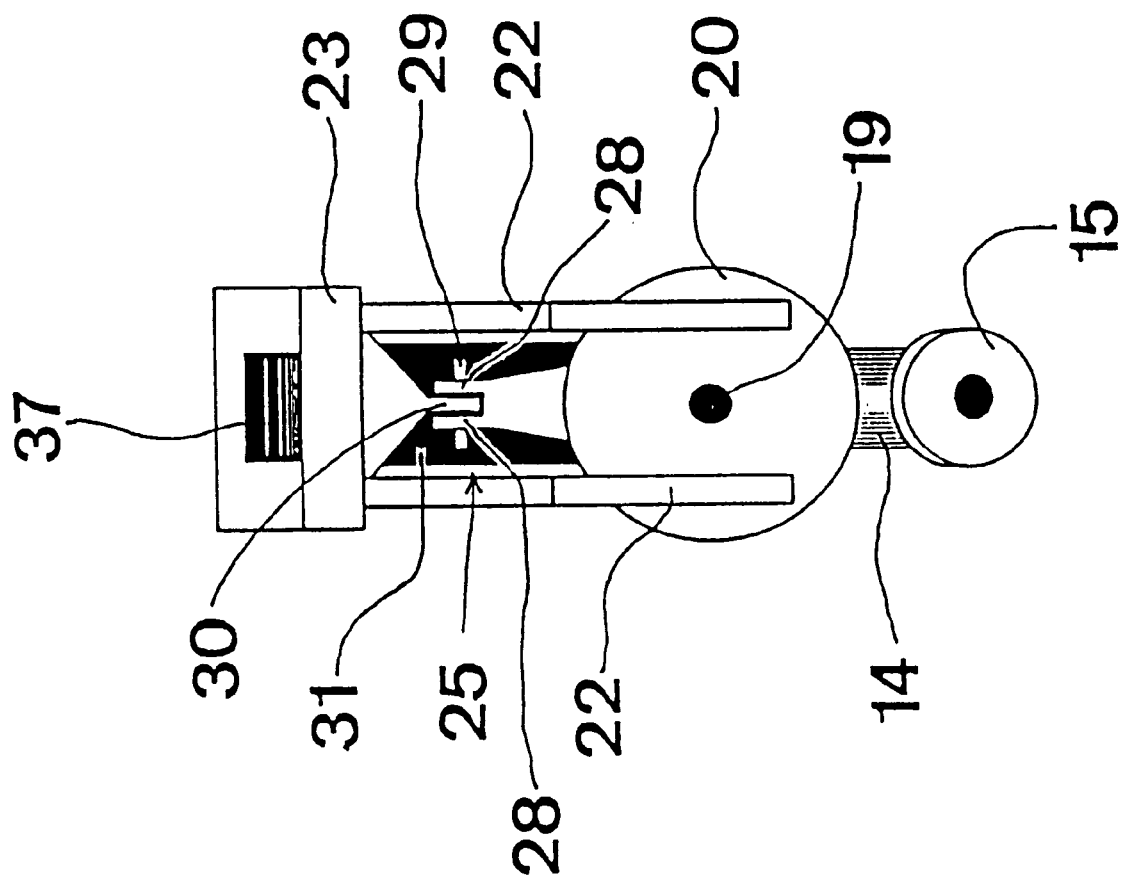
FIG. 11 shows a view from the rear, of the sealing valve from FIG. 9.

In the interest of completeness, FIG. 11 shows a view of sealing side 2 of the embodiment example shown in FIGS. 7 through 10. The blade spring, 31, and the release button, 37, may be seen distinctly.

Figure 12:
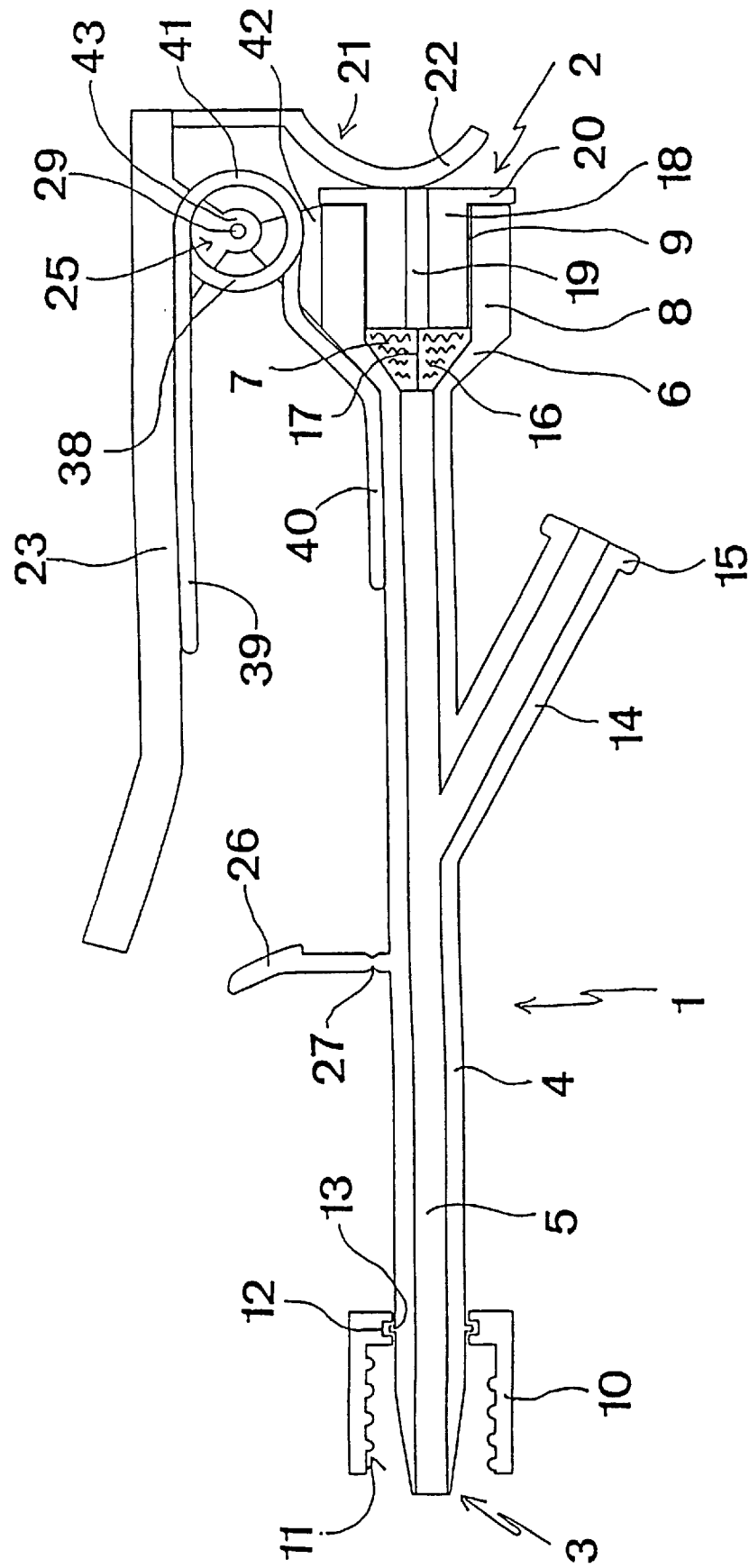
FIG. 12 shows an additional, derived embodiment example of the sealing valve.

Finally, FIG. 12 shows a cross-section view of an additional embodiment example, in which a spiral spring, 38, serves as the spring element. This spiral spring, 38, exhibits a lever arm, 23, leg, 39, and a valve body leg, 40, applied to valve body 1, as well as windings, 41, that surround the articulated pin, 29. The articulated pin, 29, is held by two articulated struts, 42, applied to sealing cylinder 8 on the side of spiral spring 38. Two articulated grommets, 43, that are attached to lever arm 23, are mounted onto the articulated pin, 29, so as to swivel, to the side of the spiral spring, 38. As in the case of the embodiment example depicted in FIGS. 1 through 3, the lever arm, 23, may be arrested by means of a snap hook, 26.

Finally, it should be noted that in addition to the derivations of the spring mechanism, additional derivations, especially of valve body 1, are possible. It is possible, for example, to position the sealing cylinder 8 immediately next to the main tube 4, without the conical extension, 6, so that a contact surface for a sealing plug, which surface runs oblique to the longitudinal axis, results. This embodiment form has the advantage of greater simplicity.

An additional possibility is to use a sealing cylinder that exhibits the same internal diameter as that of the main tube, 4. In the case of such an embodiment example, a sealing plug can be held by a ring-shaped adhesive point in the sealing cylinder. Another possibility is to provide, on a sealing plug, a ridge that runs in the direction of the circumference that engages a groove that runs around the circumference of the inside of sealing cylinder 8. In this case, however, the side of the sealing plug that is exposed to the fluid that is to be sealed off may not be selected so as to be too large, because otherwise, the spring element must apply a counteractive pressure of too great a strength.

I claim:

1. A sealing valve for use with catheters, said valve comprising:
    A valve body, said body including a connecting end and a sealing end and a passage interconnecting said connecting end and said sealing end;
    a movable sealing plug disposed in said passage for sealing said passage, said sealing plug including a plug passage;
    a compressing element operably associated with said sealing plug;
    a spring for urging said compressing element against said sealing plug and for moving said plug into sealing engagement with said passage; and
    a neutralizing element for preventing said spring from urging said compressing element from moving said plug into sealing engagement with said passage.

2. The sealing valve according to claim 1 wherein said body comprises a hollow tubular body and a hollow sealing cylinder, said plug disposed in said sealing cylinder, the inside diameter of said sealing cylinder being greater than the inside diameter of said tubular body.

3. The sealing valve according to claim 2 wherein the body further comprises a conical transition passage interconnecting the tubular body passage portion and the sealing cylinder passage portion, said sealing plug disposed in said conical transition passage.

4. The sealing valve according to claim 1 wherein said compressing element comprises a compression piston having a piston passage therein, said piston passage aligned with said plug passage when said compressing element is urged against said sealing plug.

5. The sealing valve according to claim 4 wherein said compressing element further comprises a lever which is pivotally mounted on said valve body.

6. The sealing valve according to claim 1 wherein said spring comprises a helical compression spring.

7. The sealing valve according to claim 1 wherein said spring comprises a spiral spring.

8. The sealing valve according to claim 5 wherein said spring comprises a leaf spring.

9. The sealing valve according to claim 5 wherein said neutralizing element comprises a snap hook which is engageable with said lever to prevent said spring from urging said compressing element from moving said plug into sealing engagement with said passage.

10. The sealing valve according to claim 8 further including a guide groove for guiding said leaf spring.

11. The sealing valve according to claim 8 wherein said leaf spring further comprises a bent leaf spring portion, said lever including an aperture for engagement with said bent leaf spring portion for preventing said spring from urging said compressing element from moving said plug into sealing engagement with said passage.

12. The sealing valve according to claim 11 further including a tappet and a tappet actuating button for causing said vent portion to be moved out of said aperture.

* * * * *